United States Patent
Chang et al.

(10) Patent No.: US 7,417,050 B2
(45) Date of Patent: Aug. 26, 2008

(54) HETEROCYCLIC COMPOUNDS

(75) Inventors: Hui-Fang Chang, Wilmington, DE (US); Eifion Phillips, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 161 days.

(21) Appl. No.: 10/511,525

(22) PCT Filed: Apr. 15, 2003

(86) PCT No.: PCT/SE03/00615

§ 371 (c)(1),
(2), (4) Date: Oct. 15, 2004

(87) PCT Pub. No.: WO03/087104

PCT Pub. Date: Oct. 23, 2003

(65) Prior Publication Data

US 2005/0131003 A1    Jun. 16, 2005

(30) Foreign Application Priority Data

Apr. 18, 2002  (SE)  ..................... 0201185
Dec. 4, 2002  (SE)  ..................... 0203606

(51) Int. Cl.
*A61K 31/44* (2006.01)
*C07D 401/04* (2006.01)
(52) U.S. Cl. ........................ 514/279; 546/18
(58) Field of Classification Search ............ 546/18; 514/278, 279
See application file for complete search history.

(56) References Cited

U.S. PATENT DOCUMENTS

| 6,110,914 | A  | * | 8/2000  | Phillips et al. | ............ | 514/233.2 |
| 6,569,865 | B2 | * | 5/2003  | Eifion         | ............ | 514/278   |
| 6,995,167 | B2 | * | 2/2006  | Loch et al.    | ............ | 514/278   |
| 2003/0018042 | A1 |   | 1/2003 | Phillips       |              |           |
| 2003/0149065 | A1 | * | 8/2003 | Loch, III et al. | ........... | 514/278   |
| 2005/0250802 | A1 | * | 11/2005 | Loch et al.   | ............ | 514/278   |

FOREIGN PATENT DOCUMENTS

| WO | WO 9903859 |      | 1/1999  |
| WO | WO 0042044 | A1   | 7/2000  |
| WO | WO 0045846 | A1   | 8/2000  |
| WO | WO 02096912 | A1  | 12/2002 |

* cited by examiner

*Primary Examiner*—Rita J Desai
(74) *Attorney, Agent, or Firm*—Kenneth F. Mitchell

(57) ABSTRACT

Compounds of formula I:

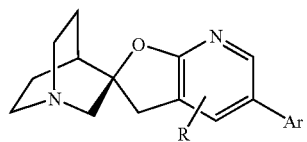

I and pharmaceutically-acceptable salts thereof, wherein Ar and R are as defined in the specification, compositions containing such compounds and the use of such compounds and compositions for use in therapy.

6 Claims, No Drawings

HETEROCYCLIC COMPOUNDS

RELATED APPLICATIONS

This is a National Stage of International Application PCT/SE03/00615, filed Apr. 15, 2003, which claims the benefit of Application No. 0201185-6, filed in Sweden on Apr. 18, 2002, and Application No. 0203606-9, filed in Sweden on Dec. 4, 2002.

TECHNICAL FIELD

This invention relates to novel spiroazabicyclic heterocyclic amines or pharmaceutically acceptable salts thereof, processes for preparing them, pharmaceutical compositions containing them and their use in therapy.

BACKGROUND OF THE INVENTION

The use of compounds which bind to nicotinic acetylcholine receptors for the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is discussed in McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; and in Williams et al., (1994) "Neuronal Nicotinic Acetylcholine Receptors," Drug News & Perspectives, vol. 7, pp. 205-223.

DESCRIPTION OF THE INVENTION

This invention comprises compounds that are potent ligands for nicotinic acetylcholine receptors (nAChR's).

Compounds of the invention are those in accord with formula I:

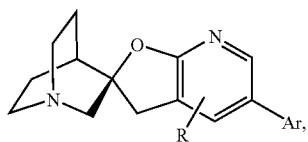

I and pharmaceutically-acceptable salts thereof, wherein:

Ar is either a monocyclic 5-membered ring heterocycle or a bicyclic benzo-fused 5-membered ring heterocycle connected via the 5-membered ring, having, as part of the five membered ring one ring nitrogen atom and either one ring oxygen atom or one ring sulfur atom, said monocyclic or fused bicyclic ring heterocycle being substituted with 0, 1, or 2 substitutents selected from $C_{1-4}$ alkyl, $C_{1-4}$ alkoxy, $C_{1-4}$ halogenated alkyl, $C_{1-4}$ oxygenated alkyl, $C_{2-4}$alkenyl, $C_{2-4}$alkynyl, halogen, —$CO_2R^1$, —$C(O)R^1$, —CN, —$NO_2$, —$(CH_2)_nNR^1R^2$ n is 0, 1, or 2

$R^1$ and $R^2$ are independently selected at each occurrence from hydrogen or $C_{1-4}$alkyl R is a substituent selected from hydrogen, $C_{1-4}$alkyl, $C_{1-4}$ halogenated alkyl, $C_{1-4}$ oxygenated alkyl, or halogen.

Particular compounds of the invention are those wherein R is hydrogen and Ar is a 5-membered ring heterocycle having one ring nitrogen atom and either one ring oxygen atom or one ring sulfur atom and having 0 or 1 substituents selected from methyl, ethyl, or halogen.

Other particular compounds of the invention are those wherein R is hydrogen and Ar is a 9-membered ring fused bicyclic heterocycle having one ring nitrogen atom and either one ring oxygen atom or one ring sulfur atom and having 0 or 1 substituents selected from methyl, ethyl, or halogen.

Particular compounds of the invention include:
(2'R)-5'-(thiazol-5-yl)spiro[1-azabicyclo[2.2.2]octane-3,2'(3'H)-furo[2,3-b]pyridine];
(2'R)-5'-(thiazol-4-yl)spiro[1-azabicyclo[2.2.2]octane-3,2'(3'H)-furo[2,3-b]pyridine];
(2'R)-5'-(thiazol-2-yl)spiro[1-azabicyclo[2.2.2]octane-3,2'(3'H)-furo[2,3-b]pyridine];
(2'R)-5'-(2-methylthiazol-4-yl)spiro[1-azabicyclo[2.2.2]octane-3,2'(3'H)-furo[2,3-b]pyridine];
(2'R)-5'-(benzothiazol-2-yl)spiro[1-azabicyclo[2.2.2]octane-3,2'(3'H)-furo[2,3-b]pyridine];
(2'R)-5'-(oxazol-2-yl)spiro[1-azabicyclo[2.2.2]octane-3,2'(3'H)-furo[2,3-b]pyridine];
(2'R)-5'-(benzoxazol-2-yl)spiro[1-azabicyclo[2.2.2]octane-3,2'(3'H)-furo[2,3-b]pyridine];
(2'R)-5'-(3,5-dimethylisoxazol-4-yl)spiro[1-azabicyclo[2.2.2]octane-3,2'(3'H)-furo[2,3-b]pyridine].

Other particular compounds of the invention include:
(2'R)-5'-(2-trifluoromethylthiazol-4-yl)spiro[1-azabicyclo[2.2.2]octane-3,2'(3'H)-furo[2,3-b]pyridine];
(2'R)-5'-(2-methylthiazol-5-yl)spiro[1-azabicyclo[2.2.2]octane-3,2'(3'H)-furo[2,3-b]pyridine];
(2'R)-5'-(2-trifluoromethylthiazol-5-yl)spiro [1-azabicyclo[2.2.2]octane-3,2'(3'H)-furo[2,3-b]pyridine].

In another aspect the invention relates to compounds according to formula I and their use in therapy and compositions containing them.

In a further aspect the invention relates to compounds according to formula I wherein one or more of the atoms is labelled with a radioisotope of the same element. In a particular form of this aspect of the invention the compound of formula I is labelled with tritium In a particular aspect the invention relates to the use of compounds according to formula I for the therapy of diseases mediated through the action of nicotinic acetylcholine receptors. A more particular aspect of the invention relates to the use of compounds of formula I for the therapy of diseases mediated through the action of (α7 nicotinic acetylcholine receptors.

Another aspect of the invention relates to a pharmaceutical composition comprising a compound as described above, and a pharmaceutically-acceptable diluent or carrier.

Another aspect of the invention relates to the above pharmaceutical composition for use in the treatment of prophylaxis of human diseases or conditions in which activation of the α7 nicotinic receptor is beneficial.

Another aspect of the invention relates to the above pharmaceutical composition for use in the treatment or prophylaxis of psychotic disorders or intellectual impairment disorders.

Another aspect of the invention relates to the above pharmaceutical composition for use in the treatment or prophylaxis of Alzheimer's disease, learning deficit, cognition deficit, attention deficit, memory loss, Attention Deficit Hyperactivity Disorder, anxiety, schizophrenia, or mania or manic depression Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

Another aspect of the invention relates to a use of a compound as described above in the manufacture of a medicament for the treatment or prophylaxis of human diseases or conditions in which activation of the α7 nicotinic receptor is beneficial.

Another aspect of the invention relates to a use of a compound as described above in the manufacture of a medicament for the treatment or prophylaxis of psychotic disorders or intellectual impairment disorders.

Another aspect of the invention relates to the above use, wherein the condition or disorder is Alzheimer's disease, learning deficit, cognition deficit, attention deficit, memory loss, Attention Deficit Hyperactivity Disorder.

Another aspect of the invention relates to the above use, wherein the disorder is anxiety, schizophrenia, or mania or manic depression.

Another aspect of the invention relates to the above use, wherein the disorder is Parkinson's disease, Huntington's disease, Tourette's syndrome, or neurodegenerative disorders in which there is loss of cholinergic synapses.

Another aspect of the invention relates to the use of a compound as described above in the manufacture of a medicament for the treatment or prophylaxis of jetlag, cessation of smoking, nicotine addiction including that resulting from exposure to products containing nicotine, craving, pain, and for ulcerative colitis.

Another aspect of the invention relates to a method of treatment or prophylaxis of human diseases or conditions in which activation of the α7 nicotinic receptor is beneficial which comprises administering a therapeutically effective amount of a compound as described above.

Another aspect of the invention relates to a method of treatment or prophylaxis of psychotic disorders or intellectual impairment disorders, which comprises administering a therapeutically effective amount of a compound as described above.

Another aspect of the invention relates to the above method, wherein the disorder is Alzheimer's disease, learning deficit, cognition deficit, attention deficit, memory loss, or Attention Deficit Hyperactivity Disorder.

Another aspect of the invention relates to the above method, wherein the disorder is Parkinson's disease, Huntington's disease, Tourette's syndrome, or neurodegenerative disorders in which there is loss of cholinergic synapses.

Another aspect of the invention relates to the above method, wherein the disorder is anxiety, schizophrenia or mania or manic depression.

Another aspect of the invention relates to a method of treatment or prophylaxis of jetlag, cessation of smoking, nicotine addiction, craving, pain, and for ulcerative colitis, which comprises administering a therapeutically effective amount of a compound as described above.

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and an inert pharmaceutically acceptable carrier.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
  for tablets and dragees: lactose, starch, talc, stearic acid;
  for capsules: tartaric acid or lactose;
  for injectable solutions: water, alcohols, glycerin, vegetable oils;
  for suppositories: natural or hardened oils or waxes.

There is also provided a process for the preparation of such a pharmaceutical composition which comprises mixing the ingredients.

A further aspect of the invention is the use of a compound according to the invention, an enantiomer thereof or a pharmaceutically acceptable salt thereof, in the manufacture of a medicament for the treatment or prophylaxis of one of the below mentioned diseases or conditions; and a method of treatment or prophylaxis of one of the above mentioned diseases or conditions, which comprises administering a therapeutically effective amount of a compound according to the invention, or an enantiomer thereof or a pharmaceutically acceptable salt thereof, to a patient.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, craving, and for the treatment or prophylaxis of nicotine addiction (including that resulting from exposure to products containing nicotine).

It is also believed that compounds according to the invention are useful in the treatment and prophylaxis of ulcerative colitis.

As used herein, the term "$C_{1-4}$ alkyl" refers to a straight-chained, branched, or cyclic $C_{1-4}$alkyl group.

As used herein the term "$C_{1-4}$ halogenated alkyl" refers to a $C_{1-4}$alkyl group substituted with 1, 2, or 3 halogen atoms.

As used herein the term "$C_{1-4}$ oxygenated alkyl" refers to a $C_{1-4}$ hydroxyalkyl or $C_{1-4}$ alkoxyalkyl group.

Methods of Preparation

Methods which may be used for the synthesis of compounds of formula I include the method outlined in Scheme 1. Unless otherwise noted Ar and R in Scheme 1 are as defined above for Formula 1.

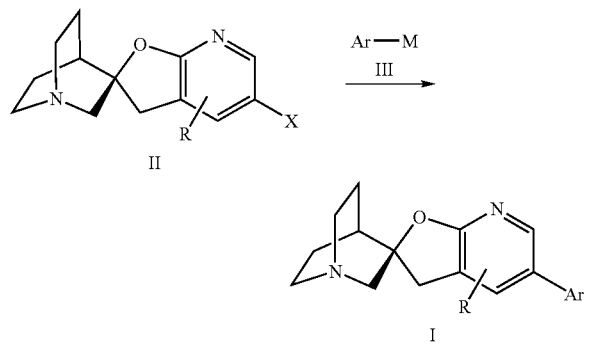

Scheme 1

Compounds of formula I may be prepared from compounds of formula II wherein X represents a halogen or $OSO_2CF_3$ substituent by reaction with an appropriate organometallic compound of formula III in the presence of a suitable organometallic catalyst and solvent. Suitable compounds of formula III include boronic acids, in which M represents $B(OH)_2$, boronic acid esters, in which M represents $B(OY)_2$, where Y represents a suitable acyclic or cyclic alkyl or aryl group, and organotin compounds, in which M represents a suitable trialkylstannyl group, for example trimethylstannyl or tri-n-butylstannyl. Suitable organometallic catalysts include palladium (0) complexes, for example tetrakis(triphenylphosphine)palladium(0) or a combination of tris(dibenzylideneacetone)dipalladium(0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula III is a boronic acid, the presence of a suitable base in addition to the other reagents is preferred. Suitable bases include sodium carbonate, cesium carbonate, and barium hydroxide. The reaction is carried out at a temperature of 0-120° C., and preferably at a temperature of 60-120° C.

Certain compounds of formula II wherein X represents halogen may be prepared from compounds of formula II wherein X represents hydrogen by reaction with a suitable halogenating agent in a suitable solvent. Suitable halogenating agents include bromine. Suitable solvents include acetic acid. The reaction is preferably performed at a temperature of 0-50 ° C., and most preferably at a temperature of 0-25° C. Compounds of formula II may be prepared by the methods described in application WO99/03859.

Compounds of formula II wherein X represents $OSO_2CF_3$ may be prepared from compounds of formula II wherein X represents OH by reaction with trifluoromethanesulfonic anhydride or other trifluoromethanesulfonylating agent in the presence of a base and a suitable solvent. Suitable bases include pyridine, and 2,6-di-t-butylpyridine. The reaction is preferably performed at a temperature of –78 to 120° C., and most preferably at a temperature of –78 to 0° C.

Compounds of formula III are commercially available, are described in the literature of synthetic organic chemistry, or may be prepared by methods known to one skilled in the art of synthetic organic chemistry. For example, compounds of formula III in which M represents $B(OH)_2$ may be prepared from suitable aromatic compounds having hydrogen or halogen groups, via conversion to the corresponding aryllithium or arylmagnesium compounds followed by reaction with trimethylborate and subsequent hydrolysis of the resulting borate ester. Similarly, suitable aromatic compounds having hydrogen or halogen groups may be converted to compounds of formula III in which M represents a trialkylstannyl group via conversion to the corresponding aryllithium or arylmagnesium compounds followed by reaction with an appropriate trialkylstannyl halide. The formation of the aryllithium or arylmagnesium compound is performed in a suitable inert solvent, for example, tetrahydrofuran. Alternatively, suitable aromatic compounds having halogen or $OSO_2CF_3$ may be converted to compounds of formula III in which M represents $B(OH)_2$ via reaction with bis(pinacolato)diboron and an organometallic catalyst, followed by hydrolysis of the resulting borate ester, or to compounds of formula III in which M represents a trialkylstannyl group via reaction with the appropriate bis(trialkyltin) in the presence of a suitable orgnometallic catalyst. The reaction is performed in a suitable inert solvent, for example tetrahydrofuran, and suitable organometallic catalyst include, for example tetrakis(triphenylphosphine). The reaction is performed at a temperature of about 0° C. to about 150° C., preferably about 20° C. to about 100° C. For typical procedures for effecting such conversions, see, for example, *Organic Syntheses*, 1963, *Coll. Vol.* 4, 68; *J. Org. Chem.* 1995, 60, 7508.

An alternative synthesis of compounds of formula I is outlined in Scheme 2. Unless otherwise noted Ar, R, M and X in Scheme 2 are as defined above for Scheme 1, and Ar and R are as defined in Formula I. The conditions for effecting the preparation described in Scheme 2 would be similar to those under which the preparations described in Scheme 1 would be performed with corresponding M and X groups.

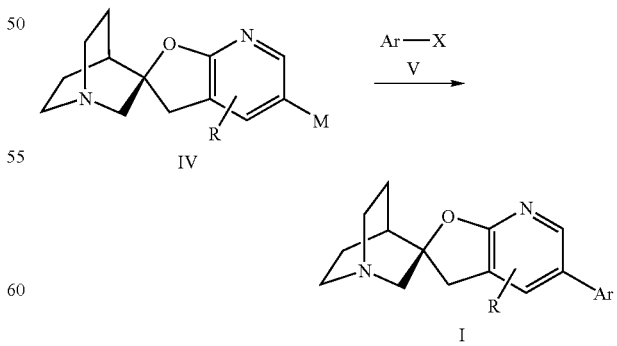

Scheme 2

Compounds of formula IV in which M represents $B(OH)_2$ may be prepared from compounds of formula II in which X is halogen, via conversion to the corresponding aryllithium or arylmagnesium compounds followed by reaction with trialkylborate and subsequent hydrolysis of the resulting borate ester. Similarly, compounds of formula IV in which M represents $SnR^3_3$ and $R^3$ represents a $C_1$-$C_6$ alkyl group may be prepared from compounds of formula II in which X is halogen, via conversion to the corresponding aryllithium or arylmagnesium compounds followed by reaction with an appropriate trialkylstannyl halide. The formation of the aryllithium or arylmagnesium compound is performed in a suitable inert solvent, for example, tetrahydrofuran, and Alternatively, compounds of formula IV in which M represents $B(OH)_2$ may be prepared from compounds of formula II in which X represents halogen or $OSO_2CF_3$ via reaction with bis(pinacolato)diboron and an organometallic catalyst, followed by hydrolysis of the resulting borate ester, and compounds of formula IV in which M represents represents $SnR^3_3$ and $R^3$ represents a $C_1$-$C_6$ alkyl group may be prepared from compounds of formula II in which X represents halogen or $OSO_2CF_3$ via reaction with the appropriate bis(trialkyltin) $R^3_3SnSnR^3_3$ in the presence of a suitable orgnometallic catalyst. The reaction is performed in a suitable inert solvent, for example tetrahydrofuiran, and suitable organometallic catalyst include, for example tetrakis(triphenylphosphine). The reaction is performed at a temperature of about 0° C. to about 150° C., preferably about 20° C. to about 100° C. For typical procedures for effecting such conversions, see, for example, *Organic Syntheses*, 1963, *Coll. Vol.* 4, 68; *J. Org. Chem.* 1995, 60, 7508.

It will be appreciated by one skilled in the art that certain optional aromatic substituents in the compounds of the invention may be introduced by employing aromatic substitution reactions, or functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalisation of an aromatic ring, for example via nitration, halogenation, or acylation; transformation of a nitro group to an amino group, for example via reduction, such as by catalytic hydrogenation; acylation, alkylation, sulfonylation of an amino or hydroxyl group; replacement of an amino group by another functional group via conversion to an intermediate diazonium salt followed by nucleophilic or free radical substitution of the diazonium salt; or replacement of a halogen by another functional group, for example via nucleophilic or organometallically-catalysed substitution reactions.

Where necessary, hydroxy, amino, or other reactive groups may be protected using a protecting group as described in the standard text "Protecting groups in Organic Synthesis", $3^{rd}$ Edition (1999) by Greene and Wuts.

The above-described reactions, unless otherwise noted, are usually conducted at a pressure of about one to about three atmospheres, preferably at ambient pressure (about one atmosphere).

Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallisation, or chiral HPLC. Alternatively the individual enantiomers may be made by reaction of the appropriate optically active starting materials under reaction conditions which will not cause racemisation.

Pharmacology

The pharmacological activity of compounds of the invention may be measured using the tests set out below:

Test A—Assay for Affinity at α7 nAChR Subtype $[^{125}I]$-α-Bungarotoxin (BTX) bindings, to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30-80 µg) were incubated with 5 nM $[^{125}I]$α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 µM (−)-nicotine, and specific binding was typically 75%.

Test B—Assay for Affinity to the α4 nAChR Subtype $[^3H]$-(−)-nicotine binding. Using a procedure modified from Martino-Barrows and Kellar (Mol Pharm (1987) 31:169-174), rat brain (cortex and hippocampus) was homogenized as in the $[^{125}I]$α-BTX binding assay, centrifuged for 20 minutes at 12,000×g, washed twice, and then resuspended in HB containing 100 µM diisopropyl fluorophosphate. After 20 minutes at 4° C., membranes (approximately 0.5 mg) were incubated with 3 nM $[^3H]$-(−)-nicotine, test drug, 1 µM atropine, and either 2 mM $CaCl_2$ or 0.5 mM EGTA for 1 h at 4° C., and then filtered over Whatman glass fiber filters (thickness C) (pretreated for 1 h with 0.5% PEI) using a Brandel cell harvester. Nonspecific binding was described by 100 µM carbachol, and specific binding was typically 84%.

Binding Data Analysis for Tests A and B $IC_{50}$ values and pseudo Hill coefficients (nH) were calculated using the non-linear curve-fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding KD values of 1.67 and 1.70 nM for the $[^{125}I]$-α-BTX and $[^3H]$-(−)-nicotine ligands respectively. Ki values were estimated using the general Cheng-Prusoff equation:

$K_i = [IC_{50}]/((2+([\text{ligand}]/[K_D])n)1/n-1)$ where a value of n=1 was used whenever nH<1.5 and a value of n=2 was used when nH≧1.5. Samples were assayed in triplicate and were typically ±5%. Ki values were determined using 6 or more drug concentrations. The compounds of the invention are compounds with binding affinities (Ki) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

EXAMPLES

Commercial reagents were used without further purification. n-Butyllithium was used as a solution in hexane. Mass spectra were recorded using an HPLC-MS system employing a HP-1100 HPLC and a Micromass LCZ Mass Spectrometer using APCI as the ionization technique, and are reported as m/z for the parent molecular ion. Room temperature refers to 20-25° C. 5'-Bromospiro[1-azabicyclo[2.2.2]octane-3,2'(3'H)-furo[2,3-b]pyridine] and other precursors were prepared as described in international patent application WO 99/03859. Radiolabelled forms of compounds of the examples are useful in a screen for the discovery of novel medicinal compounds which bind to and modulate the activity, via agonism, partial agonism, or antagonism, of the α7 nicotinic acetylcholine receptor. Such radiolabelled compounds are synthesized either by incorporating radiolabelled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Example 1

(2'R)-5'-(Thiazol-5-yl)spiro[1-azabicyclo[2.2.2]octane-3,2'(3'H)-furo[2,3-b]pyridine]

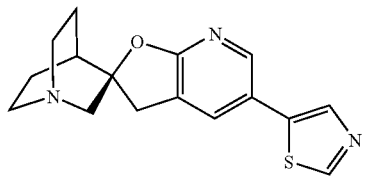

(a) 5-Tri-n-butylstannylthiazole n-Butyllithium (1.6M, 4.95 mL, 7.88 mmol) was added to a solution of 2-trimethylsilylthiazole (826 mg, 5.25 mmol) in anhydrous ether (45 mL) stirred at −78° C. under nitrogen. After 20 min, tri-n-butylstannyl chloride (2.57 g, 7.88 mmol) was added, then the solution was allowed to warm to room temperature, and stirred for another 1 h. The mixture was quenched and washed with 1N sodium hydroxide, dried through MgSO₄, and then the solvent was evaporated to give a brown oily residue. The residue of 2-trimethylsilyl-5-tributylstannyl-thiazole was passed through a column of neutral alumina eluting with a gradient of ammoniated methanol in chloroform to give the sub-title compound as a yellow oil (1.5 g).

(b) (2'R)-5'-(Thiazol-5-yl)spiro[1-azabicyclo[2.2.2]octane-3,2'(3'H)-furo[2,3-b]pyridine]

(2'R)-5'-Bromospiro[1-azabicyclo[2.2.2]octane-3,2'(3'H)-furo[2,3-b]pyridine] (89 mg, 0.3 mmol), 5-tri-n-butylstannylthiazole (390 mg, 1.05 mmol) and tetrakis(triphenylphosphine)palladium (0) (36 mg, 0.03 mmol) were dissolved in toluene (6 mL) and sealed under nitrogen. The mixture was stirred and microwaved at 135° C. under nitrogen for 8 min. The mixture was filtered through diatomaceous earth. The filtrate was diluted with chloroform, and the chloroform layer solution was washed with saturated sodium bicarbonate, dried through MgSO₄, then filtered, and evaporated. The compound was purified by flash chromatography using a gradient of ammoniated methanol in chloroform, followed by reverse phase HPLC on a Waters Novapak-HR $C_{18}$ Column using a gradient of 0-65% acetonitrile/water (each solvent containing 0.1% trifluoroacetic acid as a buffer) as the eluant. The product-containing collections were evaporated. The residue was dissolved in methanol, then excess 1N hydrochloric acid was added, and the solvent was evaporated to give the dihydrochloride salt of the title compound (79 mg) as a colourless solid; m/e 300 (MH⁺).

Example 2

(2'R)-5'-(Thiazol-4-yl)spiro[1-azabicyclo[2.2.2]octane-3,2'(3'H)-furo[2,3-b]pyridine]

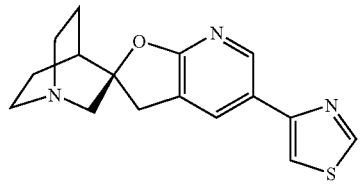

(a) 4-Tri-n-butylstannylthiazole n-Butyllithium (1.6M, 3.1 mL, 4.94 mmol) was added to a solution of 2,4-dibromothiazole (1 g, 4.12 mmol) in anhydrous ether (25 mL) stirred at −78° C. under nitrogen. After 15 min, chlorotrimethylsilane (493 mg, 4.53 mmol) was added, then the solution was allowed to warm to room temperature, and stirred for another 1 h. The mixture was quenched, and washed with 1N sodium hydroxide, dried through MgSO₄, and then the solvent was evaporated to give a brown oily residue (905 mg). The residue was purified by the distillation to give 4-bromo-2-trimethylsilylthiazole (650 mg) as a light-brown oil. Under nitrogen, the 4-bromo-2-trimethylsilylthiazole (340 mg, 1.44 mmol) was then dissolved in anhydrous ether (15 mL), and the resulting solution was stirred at −78° C. n-Butyllithium (1.5M, 1.4 mL, 2.16 mmol) was added, and the resulting solution was stirred at −78° C. for 30 minutes. Tri-n-butylstannyl chloride (703 mg, 2.16 mmol) was added, then the solution was allowed to warm to room temperature, and stirred for another 1 h. The mixture was quenched and washed with 1N sodium hydroxide, dried through MgSO₄, and then the solvent was evaporated to give a brown oily residue. The residue of 2-trimethylsilyl-4-tri-n-butylstannylthiazole was passed through a column of neutral alumina eluting with a gradient of ammoniated methanol in chloroform to give the sub-title compound, 4-tri-n-butylstannylthiazole as a yellow oil (330 mg).

(b) (2'R)-5'-(Thiazol-4-yl)spiro[1-azabicyclo[2.2.2]octane-3,2'(3'H)-furo[2,3-b]pyridine]

Prepared by a method analogous to that described for the preparation of Example 1 from (2'R)-5'-bromospiro[1-azabicyclo[2.2.2]octane-3,2'(3'H)-furo[2,3-b]pyridine] and 4-tri-n-butylstannylthiazole. The compound was isolated as the dihydrochloride salt which was a colourless solid; m/e 300 (MH$^+$).

Example 3

(2'R)-5'-(Thiazol-2-yl)spiro[1-azabicyclo[2.2.2]octane-3,2'(3'H)-furo[2,3-b]pyridine]

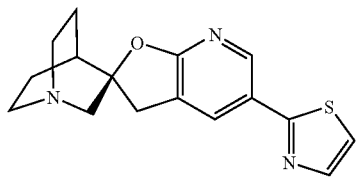

(a) 2-Tri-n-butylstannylthiazole n-Butyllithium (1.6M, 5.3 mL, 8.37 mmol) was added to a solution of thiazole (450 mg, 5.23 mmol) in anhydrous ether (30 mL) stirred −78° C. under nitrogen. After 30 min tri-n-butylstannyl chloride (2.73 g, 8.37 mmol) was added, then the solution was allowed to warm to room temperature, and stirred for another 1 h. The mixture was quenched and washed with 1N sodium hydroxide, dried through MgSO$_4$, and then the solvent was evaporated to give the sub-title compound a brown oily residue (2.0 g), which was used in the next step without further purification.

(b) (2'R)-5'-(Thiazol-2-yl)spiro[1-azabicyclo[2.2.2]octane-3,2'(3'H)-furo[2,3-b]pyridine]

Prepared by a method analogous to that described for the preparation of Example 1 from (2'R)-5'-bromospiro[1-azabicyclo[2.2.2]octane-3,2'(3'H)-furo[2,3-b]pyridine] and 2-tri-n-butylstannylthiazole. The title compound was isolated as the dihydrochloride salt which was a colourless solid; m/e 300 (MH$^+$).

Example 4

(2'R)-5'-(2-Methylthiazol-4-yl)spiro[1-azabicyclo[2.2.2]octane-3,2'(3'H)-furo[2,3-b]pyridine]

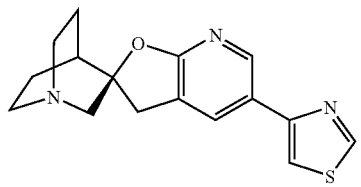

(a) 2-Methyl-4-triethylstannyl-thiazole n-Butyllithium (1.6M, 3.3 mL, 5.35 mmol) was added to a solution of 2,4-dibromothiazole (1.0 g, 4.12 mmol) in anhydrous ether (10 mL) stirred at −78° C. under nitrogen. After 20 minutes, methyl trifluromethanesulfonate (878 mg, 5.35 mmol) was added, then the reaction mixture was allowed to warm to room temperature, and stirred for another 1 h. The mixture was quenched and washed with water, washed with brine, dried through MgSO$_4$, and then the solvent was evaporated to give a brown oily residue of 2-methyl-4-bromothiazole (900 mg). Under nitrogen, the 2-methyl-4-bromothiazole (430 mg, 2.42 mmol) dissolved in anhydrous ether (5 mL) then cooled to −78° C. under nitrogen. n-Butyllithium (1.6M, 1.7 mL, 2.66 mmol) was added, followed, after 10 min by triethylstannyl bromide (760 mg, 2.66 mmol). The solution was then warmed to room temperature, and stirred for another 1 h. The mixture was quenched, and washed with 1N sodium hydroxide, dried through MgSO$_4$, and then the solvent was evaporated to give the sub-title compound give as a brown oily residue (655 mg), which was used without further purification in the next step.

(b) (2'R)-5'-(2-Methylthiazol-4-yl)spiro[1-azabicyclo[2.2.2]octane-3,2'(3'H)-furo[2,3-b]pyridine]

Prepared by a method analogous to that described for the preparation of Example 1 from (2'R)-5'-bromospiro[1-azabicyclo[2.2.2]octane-3,2'(3'H)-furo[2,3-b]pyridine] and 2-methyl-4-triethylstannyl-thiazole. The title compound was obtained as a colourless solid; m/e 314 (MH$^+$).

Example 5

(2'R)-5'-(Benzothiazol-2-yl)spiro[1-azabicyclo[2.2.2]octane-3.2'(3'H)-furo[2,3-b]pyridine]

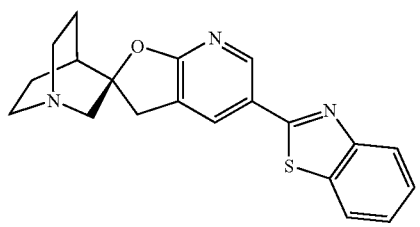

(a) 2-Tri-n-butylstannylbenzothiazole n-Butyllithium (1.6M, 10 mL, 15.98 mmol) was added to a solution of benzothiazole (1.80 g, 13.3 mmol) in anhydrous ether (30 ml) stirred at −78° C. under nitrogen. After 10 min, tri-n-butylstannyl chloride (4.33 g, 13.31 mmol) was added, then the solution was allowed to warm to room temperature, and stirred for another 1 h. The mixture was quenched and washed with 1N sodium hydroxide, dried through MgSO$_4$, filtered, and evaporated to give the sub-title compound as a brown oily residue (5.0 g), which was used without further purification in the next step.

(b) (2'R)-5'-(Benzothiazol-2-yl)spiro[1-azabicyclo[2.2.2]octane-3,2'(3'H)-furo[2,3-b]pyridine]

Prepared by a method analogous to that described for the preparation of Example 1 from (2'R)-5'-bromospiro[1-azabicyclo[2.2.2]octane-3,2'(3'H)-furo[2,3-b]pyridine] and 2-tri-n-butylstannylbenzothiazole. The title compound was obtained as a colourless solid; m/e 350 (MH$^+$).

Example 6

(2'R)-5'-(Oxazol-2-yl)spiro[1-azabicyclo[2.2.2]octane-3,2'(3'H)-furo[2,3-b]pyridine]

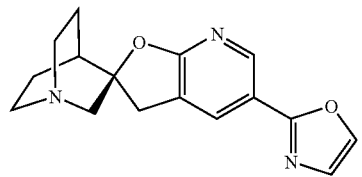

(a) 2-Triethylstannyloxazole n-Butyllithium (1.6M, 11 mL, 17.38 mmol) was added to a solution of oxazole (1.0 g, 14.48 mmol) in anhydrous ether (20 mL) stirred at −78° C. under nitrogen. After 5 min, triethylstannyl bromide (2.07 g, 7.24 mmol) was added, then the reaction mixture was allowed to warm to room temperature, and stirred for another 1 h. The mixture was quenched, and washed with 1N sodium hydroxide, dried through MgSO$_4$, and then the solvent was evaporated to give the sub-title compound as a brown oily residue (1.0 g), which was used without further purification in the next step.

(b) (2'R)-5'-(Oxazol-2-yl)spiro[1-azabicyclo[2.2.2]octane-3,2'(3'H)-furo[2,3-b]pyridine]

Prepared by a method analogous to that described for the preparation of Example 1 from (2'R)-5'-bromo-spiro[1-azabicyclo[2.2.2]octane-3,2'(3'H)-furo[2,3-b]pyridine] and 2-triethylstannyloxazole. The dihydrochloride salt of the title compound was obtained as a colourless solid; m/e 284 (MH$^+$).

Example 7

(2'R)-5'-(Benzoxazol-2-yl)spiro[1-azabicyclo[2.2.2]oxtane-3,2'(3'H)-furo[2,3-b]pyridine]

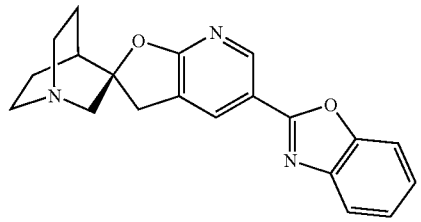

(a) 2-Triethylstannylbenzoxazole n-Butyllithium (1.6M, 6.0 mL, 9.57 mmol) was added to a solution of benzoxazole (950 mg, 7.98 mmol) in anhydrous ether (20 mL) stirred at −78° C. under nitrogen. After 10 min, triethylstannyl bromide (2.28 g, 7.98 mmol) was added, then the reaction mixture was allowed to warm to room temperature, and stirred for another 1 h. The mixture was quenched, and washed with 1N sodium hydroxide, dried through MgSO$_4$, and then the solvent was evaporated to give the sub-title compound as a brown oily residue which was used directly without further purification for the next step.

(b) (2'R)-5'-(Benzoxazol-2-yl)spiro[1-azabicyclo[2.2.2]octane-3,2'(3'H)-furo[2,3-b]pyridine]

Prepared by a method analog to that described for the preparation of Example 1 from (2'R)-5'-bromospiro[1-azabicyclo[2.2.2]octane-3,2'(3'H)-furo[2,3-b]pyridine] and 2-triethylstannylbenzoxazole. The dihydrochloride salt of the title compound was obtained as a colourless solid; m/e 343 (MH$^+$).

Example 8

(2'R)-5'-(3,5-Dimethylisoxazol-4-yl)spiro[1-azabicyclo[2.2.2]octane-3,2'(3'H)-furo[2,3-b]pyridine]

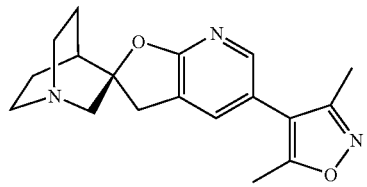

(2'R)-5'-Bromospiro[1-azabicyclo[2.2.2]octane-3,2'(3'H)-furo[2,3-b]pyridine] (200 mg, 0.68 mmol), and 3,5-dimethylisoxazole-4-boronic acid (106 mg, 0.75 mmol), tetrakis(triphenylphosphine)palladium (0) (20 mg, 0.017 mmol) and sodium carbonate (305 mg, 2.21 mmol) were placed in a sealed tube under nitrogen. Water (1.2 mL), ethanol (1.5 mL) and ethylene glycol dimethyl ether (5.5 mL) was added. The mixture was stirred and heated at 100° C. under nitrogen overnight. The mixture was filtered through diatomaceous earth. The filtrate was diluted with chloroform, washed with saturated sodium bicarbonate, dried through MgSO$_4$, and then the solvent was evaporated. The compound was purified by flash chromatography using a gradient of ammoniated methanol in chloroform followed by reverse phase HPLC on a Waters Novapak-HR C$_{18}$ Column using a gradient of 0-65% acetonitrile/water (each solvent containing 0.1% trifluoroacetic acid as a buffer) as the eluant. The product-containing collections were evaporated. The residue was dissolved in methanol, then excess 1N hydrochloric acid was added, and the solvent was evaporated to give the dihydrochloride salt of the title compound (75 mg) as a white solid; m/e 313 (MH$^+$).

The invention claimed is:

1. A compound having the formula:

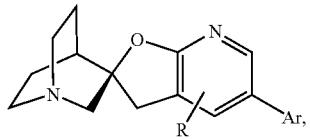

I and pharmaceutically-acceptable salts thereof, wherein

Ar is either a monocyclic 5-membered ring heterocycle or a bicyclic benzo-fused 5-membered ring heterocycle connected via the 5-membered ring, having, as part of the five membered ring one ring nitrogen atom and either one ring oxygen atom or one ring sulfur atom, said monocyclic or fused bicyclic ring heterocycle being substituted with 0, 1, or 2 substitutents selected from C$_{1-4}$ alkyl, C$_{1-4}$ alkoxy, C$_{1-4}$ halogenated alkyl, C$_{1-4}$ oxygenated alkyl, C$_{2-4}$ alkenyl, C$_{2-4}$ alkynyl, halogen, —CO$_2$R$^1$, —C(O)R$^1$, —CN, —NO$_2$, —(CH$_2$)$_n$NR$^1$R$^2$ n is 0, 1, or 2

R$^1$ and R$^2$ are independently selected at each occurrence from hydrogen or C$_{1-4}$ alkyl R is a substitutent selected from hydrogen, C$_{1-4}$ alkyl, C$_{1-4}$ halogenated alkyl, C$_{1-4}$ oxygenated alkyl, or halogen.

2. A compound according to claim 1 or a pharmaceutically-acceptable salt thereof, wherein:

Ar is a 5-membered ring heterocycle having one ring nitrogen atom and either one ring oxygen atom or one ring sulfur atom and having 0 or 1 substituents selected from methyl, ethyl, or halogen, and R is hydrogen.

3. A compound according to claim 1, selected from:
(2'R)-5'-(thiazol-5-yl)spiro[1-azabicyclo[2.2.2]octane-3,2'(3'H)-furo[2,3-b]pyridine];
(2'R)-5'-(thiazol-4-yl)spiro[1-azabicyclo[2.2.2]octane-3,2'(3'H)-furo[2,3-b]pyridine];
(2'R)-5'-(thiazol-2-yl)spiro[1-azabicyclo[2.2.2]octane-3,2'(3'H)-furo[2,3-b]pyridine];
(2'R)-5'-(2-methylthiazol-4-yl)spiro[1-azabicyclo[2.2.2]octane-3,2'(3'H)-furo[2,3-b]pyridine];
(2'R)-5'-(benzothiazol-2-yl)spiro[1-azabicyclo[2.2.2]octane-3,2'(3'H)-furo[2,3-b]pyridine];
(2'R)-5'-(oxazol-2-yl)spiro[1-azabicyclo[2.2.2]octane-3,2'(3'H)-furo[2,3-b]pyridine];
(2'R)-5'-(benzoxazol-2-yl)spiro[1-azabicyclo[2.2.2]octane-3,2'(3'H)-furo[2,3-b]pyridine];
(2'R)-5'-(3,5-dimethylisoxazol-4-yl)spiro[1-azabicyclo[2.2.2]octane-3,2'(3'H)-furo[2,3-b]pyridine];
(2'R)-5'-(2-trifluoromethylthiazol-4-yl)spiro[1-azabicyclo[2.2.2]octane-3,2'(3'H)-furo[2,3-b]pyridine];
(2'R)-5'-(2-methylthiazol-5-yl)spiro[1-azabicyclo[2.2.2]octane-3,2'(3'H)-furo[2,3-b]pyridine]; or
(2'R)-5'-(2-trifluoromethylthiazol-5-yl)spiro[1-azabicyclo[2.2.2]octane-3,2'(3'H)-furo[2,3-b]pyridine].

4. A pharmaceutical composition comprising a compound according to claim 1, and a pharmaceutically-acceptable diluent or carrier.

5. A compound according to claim 1, wherein one or more of the atoms is a radioisotope of the element.

6. A compound according to claim 5, wherein the radioisotope is tritium.

* * * * *